United States Patent
Goddard

[11] 3,992,189
[45] Nov. 16, 1976

[54] HERBICIDAL ISOINDOL-1-ONE DERIVATIVES

[75] Inventor: Steven Jerome Goddard, West Grove, Pa.

[73] Assignee: E. I. Du Pont de Nemours & Company, Wilmington, Del.

[22] Filed: Oct. 31, 1975

[21] Appl. No.: 627,887

[52] U.S. Cl............................. 71/96; 260/325 PH; 260/376 HL
[51] Int. Cl.².................. A01N 9/22; C07D 209/46
[58] Field of Search .................. 260/325 PH; 71/96

[56] References Cited
UNITED STATES PATENTS

| | | | |
|---|---|---|---|
| 3,818,037 | 6/1974 | Schefczik...................... | 260/325 PH |
| 3,849,438 | 11/1974 | Houlihan et al.............. | 260/325 PH |
| 3,890,346 | 6/1975 | Iobal............................ | 260/325 PH |

FOREIGN PATENTS OR APPLICATIONS

2,119,703   7/1972   France.......................... 260/326 HL

*Primary Examiner*—Elbert L. Roberts
*Assistant Examiner*—S. P. Williams

[57] ABSTRACT

This invention relates to herbicidal isoindol-1-one derivatives. These compounds have the general formulae:

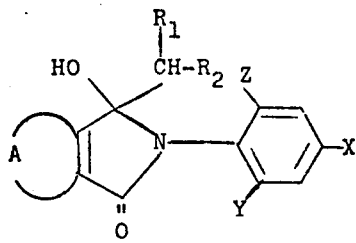

Formula I

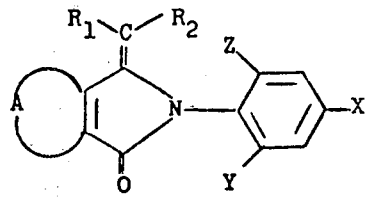

Formula IIa

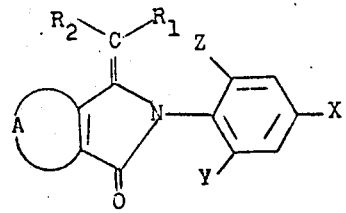

Formula IIb wherein
 $R_1$ is hydrogen or methyl;
 $R_2$ is hydrogen or alkyl of 1 to 4 carbons;
 X is fluorine, chlorine or bromine;
 Y is hydrogen or fluorine;
 Z is hydrogen or fluorine, provided that when Y and Z are both fluorine, X must also be fluorine; and
 A is $-(CH_2)_4-$ or $-CH=CH-CH=CH-$, provided that when A is $-CH=CH-CH=CH-$ and Y is hydrogen, Z must be fluorine.

Both geometric isomers, Formulae II*a* and II*b*, are encompassed by this invention.

In particular, these compounds have demonstrated that they are active pre- and post-emergence herbicides and tend to do minimal damage to certain desirable crops, e.g., corn and wheat.

18 Claims, No Drawings

HERBICIDAL ISOINDOL-1-ONE DERIVATIVES

BACKGROUND OF THE INVENTION

A number of isoindole-type compounds are known in the prior art. Recently, in German Offenlegungsschrift No. 2,165,651, a group of isoindol-1,3-diones which are useful as herbicides was disclosed. The general formula for the isoindol-1,3-diones is as follows:

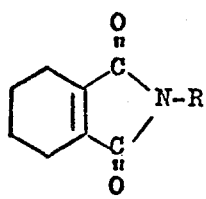

wherein R may be an aryl, aralkyl or benzyl optionally substituted with 1 to 5 halogen atoms; hydroxy, nitro, cyano, thiocyano, carboxy, halogenated alkyl, or alkyl, or alkoxy, lower alkylthio, phenyl groupings and a group having the configuration —O—CH$_2$A may also be substituted therein, wherein A is a phenyl or a naphthyl group, wherein the phenyl group may have one or more substitutions therein, such as halogen atoms, nitro groupings, lower alkyl groupings or lower alkoxy groupings.

Typical of the compounds disclosed in the Offenlegungsschrift is the compound of Example 1:

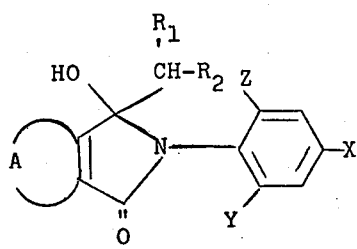

Although herbicides such as the herbicide discussed above have proven effective in controlling undesired vegetation there is a constant need for improved herbicides because of the current critical food shortages in the world. Any improvement in herbicidal activity, in conjunction with no significant damage to the crop which is to be protected, is desirable. Consequently, it is readily apparent that there is a continuing need for improved herbicides.

According to the instant invention, novel, improved herbicides have been discovered.

SUMMARY OF THE INVENTION

This invention relates to the novel compounds of Formulae I, IIa and IIb, and to their use as herbicides.

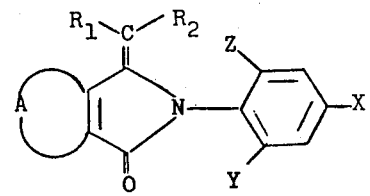

Formula I                        Formula IIa

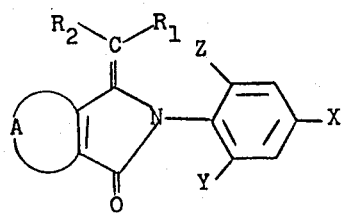

Formula IIb wherein
$R_1$ is hydrogen or methyl;
$R_2$ is hydrogen or alkyl of 1 to 4 carbons;
X is fluorine, chlorine or bromine;
Y is hydrogen or fluorine;
Z is hydrogen or fluorine, provided that when Y and Z are both fluorine, X must also be fluorine; and A is —(CH$_2$)$_4$— or —CH=CH—CH=CH—, provided that when A is —CH=CH—CH=CH— and Y is hydrogen, Z must be fluorine.

Both geometric isomers, Formulae IIa and IIb, are encompassed by this invention.

The preferred compounds are those of Formula IIa or IIb.

More preferred compounds for their high degree of herbicidal activity, are the compounds of Formula II wherein Z is fluorine and A is -(CH$_2$)$_4$—.

More highly preferred are those compounds of Formula II wherein R$_1$ is hydrogen, Z is fluroine, and A is —(CH$_2$)$_4$—.

Most preferred for their high degree of herbicidal activity and/or ease of synthesis are those compounds of Formula II wherein R$_1$ and R$_2$ are hydrogen, Z is fluorine, and A is —(CH$_2$)$_4$—.

Specifically preferred is the compound 2-(4-chloro-2-fluorophenyl)-2,3,4,5,6,7-hexahydro-3-methylene-1H-isoindol-3-one.

This invention, as indicated above, also includes herbicidal compositions containing the above compounds as active ingredients and methods of controlling undesirable vegetation by applying the compounds and/or compositions to the locus of such undesired vegetation.

SYNTHESIS OF THE COMPOUNDS

The novel compounds of Formulae I, IIa and IIb can be prepared as shown in the following reaction sequences:

GENERAL REACTIONS

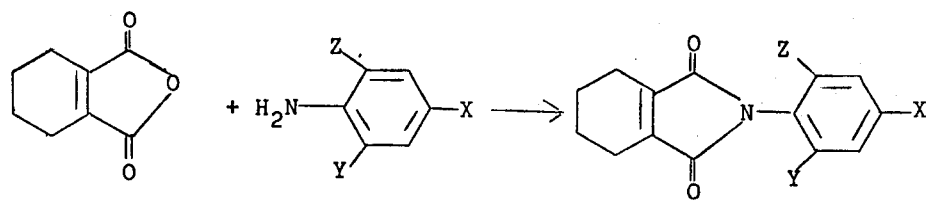

Formula (a)

Step 2

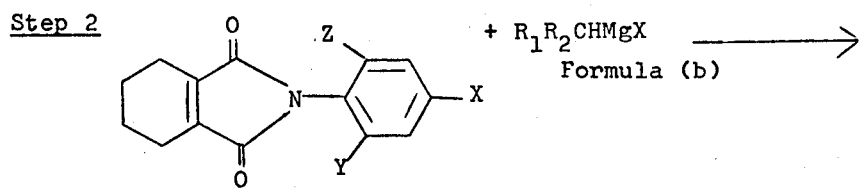

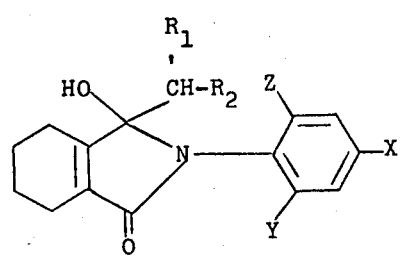

Formula I

Step 3

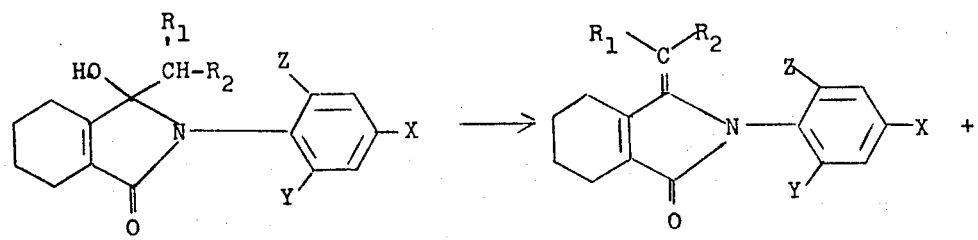

Formula I            Formula IIa

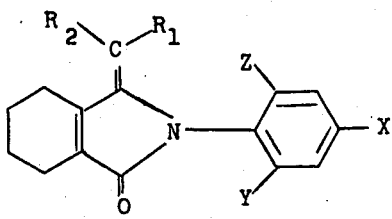

Formula IIb

Step 3(a)

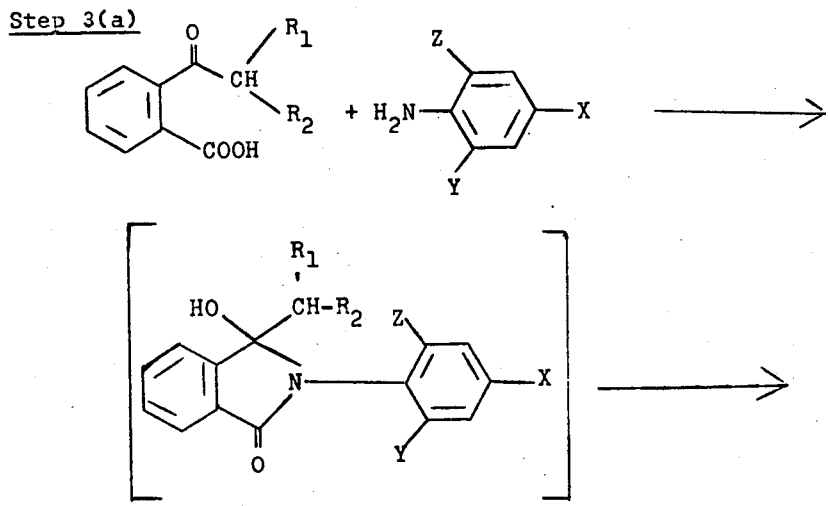

Formula I

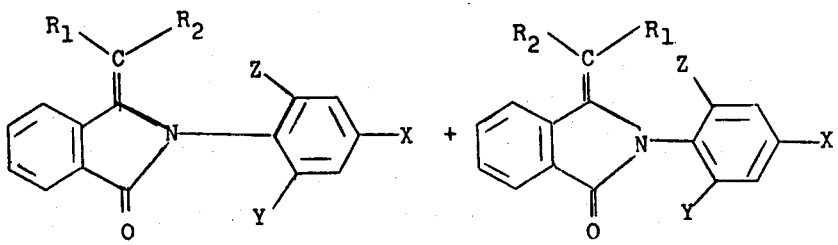

Formula IIa          Formula IIb wherein
R₁ is hydrogen or methyl;
R₂ is hydrogen or alkyl of 1 to 4 carbons;
X is fluorine, chlorine or bromine;
Y is hydrogen or fluorine;
Z is hydrogen or fluorine, provided that when Y and Z are both fluorine, X must also be fluorine.

STEP 1

The preparation of the 2-aryl-4,5,6,7-tetrahydro-2H isoindol-1,3-diones (Formula (a)) is described in Netherlands Pat. No. 7,117,690 (Mitsubishi Chem. Ind. which is herein incorporated by reference. The anilin and 3,4,5,6-tetrahydrophthalic anhydride are refluxe in glacial acetic acid at 115°–120° C and atmospheri pressure for several hours, e.g., 2–8, and the desired product, Formula (a), isolated.

STEP 2

A solution of an alkyl magnesium halide of Formula (b) in an ether (such as tetrahydrofuran) is added dropwise to a cold (−5° to +5° C) solution of a 2-aryl-4,5,6,7-tetrahydro-2H-isoindole-1,3-dione (Formula (a)) in an ether (such as tetrahydrofuran) and the reaction mixture is stirred at the reaction temperature of −5 to +5° C for several hours, e.g. 2–8. The 2-aryl-2,3,4,5,6,7-hexahydro-3-hydroxy-3-alkyl-1H-isoindol-1-one is freed of its magnesium complex by reaction with saturated aqueous ammonium chloride solution followed by filtration. Upon evaporation of the solvent from the filtrate under reduced pressure of 100–300 mm. Hg at a temperature of 25°–75° C, the 2-aryl-2,3,4,5,6,7-hexahydro-3-hydroxy-3-alkyl-1H-isoindol-1-one (Formula I) is obtained.

p-toluenesulfonic acid) is heated in a bath (such as an oil bath) at 150°–180° C and atmospheric pressure for several hours, e.g. 2–8. The reaction mixture is diluted with a water-immiscible solvent (such as chloroform) and washed sequentially with dilute aqueous acid (such as 10% aqueous hydrochloric acid), dilute aqueous base (such as 10% aqueous sodium carbonate, and saturated aqueous alkali metal salt solution (such as saturated aqueous sodium chloride solution). The 2-aryl-3-alkylidene-1H-isoindol-1-one is isolated by evaporating the solvent under reduced pressure of 100–300 mm. Hg at 25°–75° C and crystallizing the residue from a suitable solvent (such as methanol).

Certain of the anilines employed in the synthesis of the compounds of this invention are novel. 4-Chloro-2-fluoroaniline, for example, can be prepared from 2'-fluoroacetanilide [G. Schiemann and H. G. Baumgarten, Chem. Berichte 70, 1416 (1937)] by the reaction sequences shown below.

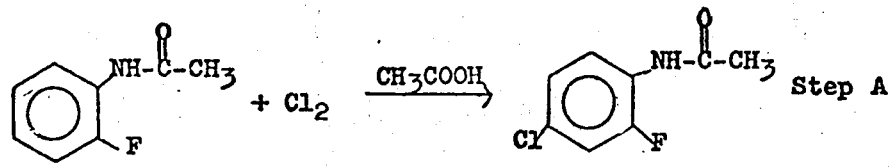
Step A

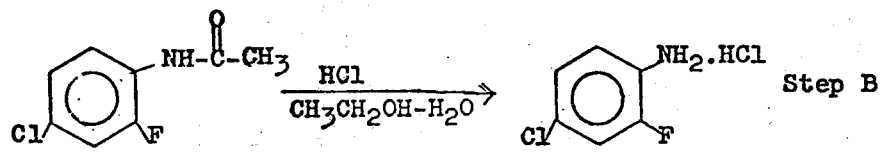
Step B

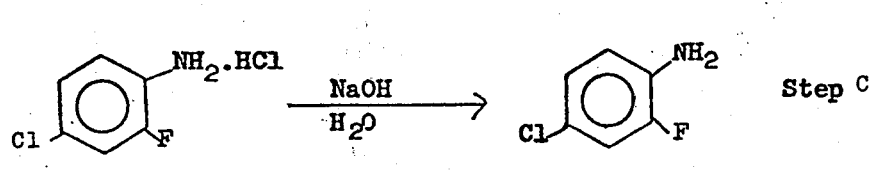
Step C

Step A

STEP 3

An acidic catalyst (such as potassium bisulfate) is added to the 2-aryl-2,3,4,5,6,7-hexahydro-3-hydroxy-3-alkyl-1H-isoindol-1-one (Formula I) from Step II and the mixture is heated with stirring to 150°–180° C in bath (such as an oil bath) for several hours, e.g. 2–8. The resulting 2-aryl-2,3,4,5,6,7-hexahydro-3-alkylidene-1H-isoindol-1-one is isolated by taking the reaction mixture up in a water-immiscible solvent (such as chloroform), washing with water, drying with a drying agent (such as anhydrous sodium sulfate) and then evaporating the solvent under reduced pressure of 100–300 mm. Hg at a temperature of 25°–75° C. When $R_1$ and $R_2$ are different both geometric isomers are formed.

STEP 3a

A mixture of a 2-acylbenzoic acid and an aniline in the presence of a catalytic amount of an acid (such as

STEP A

The chlorination of acetanilides in acetic acid is well known to those skilled in the art, and may be carried out under the conditions taught in W. W. Reed and K. J. P. Orton, J. Chem. Soc., 91, 1543 (1907) for the chlorination of acetanilide. The chlorination of 2'-fluoroacetanilide takes place at 25°–30° C over several hours (e.g. 5) at atmospheric pressure. The resulting produce is 4'-chloro- 2'-fluoroacetanilide.

STEP B

4'-Chloro-2'-fluoroacetanilide is refluxed in a mixture of a lower alcohol (50%) (e.g. ethanol) and concentrated hydrochloric acid (50%) for several hours (e.g.5 or more) at 70°–90° C and atmospheric pressure. The solvent mixture is removed at a reduced pressure of 100 to 300 mm. Hg. and 20°–50° C to leave a residue of the hydrochloride salt of 4-chloro-2-fluoroaniline.

STEP C

After basification of an aqueous solution of the hydrochloride salt of 4-chloro-2-fluoroaniline with an alkali metal hydroxide solution such as 50% sodium hydroxide at ambient conditions, the free 4-chloro-2-fluoroaniline is extracted into a suitable water-immiscible organic solvent such as ethyl ether or methylene chloride. The crude 4-chloro-2-fluoroaniline is isolated by removal of the organic solvent under reduced pressure of 100 to 300 mm. Hg at 20°–50° C.

2-Fluoro-4-bromoaniline can be prepared by bromination of 2-fluoroaniline (prepared in Chem. Berichte, 70, 1416 (1937)) with N-bromosuccinimide as shown in the following equation.

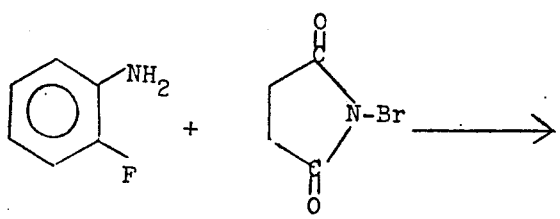

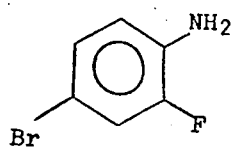

The bromination of anilines using N-bromosuccinimide in an inert organic solvent such as methylene chloride is well known to those skilled in the art, e.g., J. B. Wommack et al,, J. Het. Chem., 6, 243 (1969). The bromination of 2-fluoroaniline is an exothermic reaction that takes place at 0° C over several hours, e.g. 5 or more. The resulting reaction mixture is washed with water several times and drived with an appropriate drying agent such as anhydrous sodium sulfate. The 4-bromo-2-fluoroaniline is recovered by removal of the organic solvent under reduced pressure of 100 to 300 mm. Hg at 20°–50°.

2,4,6-Trifluoroaniline is prepared by reduction of 1,3,5-trifluoro-2-nitrobenzene [V. I. Siele and H. J. Matsuguma, U.S. Dept. Com., Office Serv., P B Rept. 145, 510, p. 1 (1960) or Chem. Abstr. 56 15394c (1962)] using the procedures described by G. Schiemann and M. Seyhan, Chem. Berichte, 70, 2396 (1937).

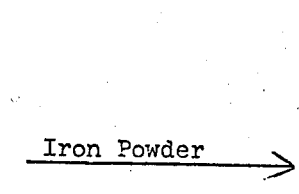

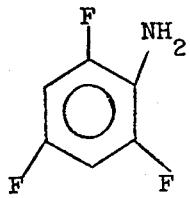

2,4-Difluoroaniline is known to the art and can be prepared by the procedure described in G. Schiemann and M. Seyhan, Chem. Berichte, 70, 2396 (1937).

The following examples further illustrate the method for synthesis of compounds of this invention. All parts are by weight and all temperatures in degrees centigrade unless otherwise indicated.

EXAMPLE 1

Preparation of 4-chloro-2-fluoroaniline

Seventy-one parts of liquid chlorine were added to a solution of 140 parts of 2'-fluoroacetanilide in 500 parts glacial acetid acid, during one hour, at 25°–27°, with ice-water cooling. While stirring for 4 hours at 25°–27°, 4'-chloro-2'-fluoroacetanilide precipitated. After collecting the product by filtration, the filtrate was poured over 2000 parts of ice. The resulting second portion of precipitated product was collected by filtration, combined with the first portion and recrystallized from 700 parts of methanol at −45° to yield 199 parts of 4'-chloro-2'-fluoroacetanilide as white crystals melting at 152°–155°.

A mixture of 119 parts of 4'-chloro-2'-fluoroacetanilide in 475 parts of ethanol and 200 parts of 37% hydrochloric acid was refluxed for 17 hours and the solvent removed under a reduced pressure of 300 mm. Hg to yield the moist, solid hydrochloride salt of 4-chloro-2-fluoroaniline.

The moist, solid hydrochloride salt of 4-chloro-2-fluoroaniline was cooled to 10° in an ice-acetone bath and 50% aqueous sodium hydroxide was added dropwise, with stirring, until pH 11 was obtained. The resulting two-phase mixture was extracted four times; 500 parts of methylene chloride were used for each extraction. The combined organic extracts were dried with anhydrous sodium sulfate and the solvent removed under reduced pressure of 300 mm. Hg to leave 89 parts of light brown, oily 4-chloro-2-fluoroaniline, $n_D^{25} = 1.5541$.

EXAMPLE 2

Preparation of 4-bromo-2-fluoroaniline

160 Parts of solid N-bromosuccinimide were added in portions over a 2 hour period to a solution of 100 parts of 2fluoroaniline in 400 parts of methylene chloride cooled to 0° C. After stirring for 20 minutes, the dark red mixture was washed four times; 200 parts of cold water were used for each washing. The red organic phase was dried with anhydrous sodium sulfate and evaporated under 300 mm. Hg to 164 parts of brown, oily 4-bromo-2-fluoroaniline, $n_D^{25}$: 1.5885.

EXAMPLE 3

Preparation of
2-(4-chloro-2-fluorophenyl-4,5,6,7-tetrahydro-2H-isoindole-1,3-dione A solution of 88 parts of 3,4,5,6-tetrahydrophthalic anhydride in 2000 parts of glacial acetic acid was treated with 84 parts of 4-chloro-2-fluoroaniline at once and stirred for one hour. After refluxing for 19 hours, 1000 parts of acetic acid were distilled from the reaction mixture. The residue from the distillation was poured over 3000 parts of ice. The resulting crystals were filtered and recrystallized from 700 parts of methanol at −40° after activated carbon treatment, to yield 117 parts off-white crystals of 2-(4-chloro-2-fluorophenyl)-4,5,6,7-tetrahydro-2H-isoindole-1,3-dione melting at 76.5–78.0°.

The following compounds can be prepared by substituting the appropriate aniline for 4-chloro-2-fluoroaniline: 2-(4-bromo-2-fluorophenyl)-4,5,6,7-tetrahydro-2H-isoindole-1,3-dione, m.p. 102.0°–102.5°

2-(2,4-difluorophenyl)-4,5,6,7-tetrahydro-2H-isoindole-1,3-dione, m.p. 73°–74°

2-(2,4,6-trifluorophenyl)-4,5,6,7-tetrahydro-2H-isoindole-1,3-dione, m.p. 91°–92°

EXAMPLE 4

Preparation of
2-(4-chloro-2-fluorophenyl)-2,3,4,5,6,7-hexa-hydro-3-hydroxy-3-methyl-1H-isoindol-1-one Twenty parts of a 3.13M methylmagnesium chloride solution in tetrahydrofuran was added dropwise to a solution of 20 parts of 2-(4-chloro-2-fluorophenyl)-4,5,6,7-tetrahydro-2H-isoindole-1,3-dione in 200 parts of anhydrous tetrahydrofuran at 0° C over ½ hour. After stirring for 2 hours at 0°, 10 parts of a saturated aqueous ammonium chloride was added dropwise at 0°, resulting in a granular precipitate. After filtering the precipitate, the filtrate was evaporated at 300 mm. Hg and 50° to give 23.5 parts of 2-(4-chloro-2-fluorophenyl) -2,3,4,5,6,7-hexahydro-3-hydroxy-3methyl-1H-isoindol-1-one as indicated in particular by adsorption in the infrared spectrum of 1690 cm$^{-1}$ (amide) and 3300 cm$^{-1}$ (hydroxyl) and in the nuclear magnetic resonance spectrum of 4.6$\delta$ (1H, hydroxyl) and 1.1$\delta$ (3H, singlet methyl).

The following compounds can be prepared by substituting the appropriate alkyl magnesium halide solution for methyl magnesium chloride solution and the appropriate 2-aryl-4,5,6,7-tetrahydro-2H-isoindol-1,3-dione:

2-(4-chloro-2-fluorophenyl)-2,3,4,5,6,7-hexahydro-3-hydroxy-3-propyl-1H-isoindol-1-one 2-(2,4,6-trifluorophenyl)-2,3,4,5,6,7-hexahydro-3-hydroxy-3-(1-methylpentyl)-1H-isoindol-1-one 2-(4-bromophenyl)-2,3,4,5,6,7-hexahydro-3-hydroxy-3-(1-methyl-ethyl)-1H-isoindol-1-one 2-(4-chlorophenyl)-2,3,4,5,6,7-hexahydro-3-hydroxy-3-methyl-1H-isoindol-1-one 2-(2,4-difluorophenyl)-2,3,4,5,6,7-hexahydro-3-hydroxy-3-n-butyl-1H-isoindol-1-one 2-(4-bromo-2-fluorophenyl)-2,3,4,5,6,7-hexahydro-3-hydroxy-3-methyl-1H-isoindol-1one 2-(4-chloro-2-fluorophenyl)-2,3,4,5,6,7-hexahydro-3-hydroxy-3-ethyl-1H-isoindol-1-one 2-(4-fluorophenyl)-2,3,4,5,6,7-hexahydro-3-hydroxy-3-n-pentyl-1H-isoindol-1-one

EXAMPLE 5

Preparation of
2-(4-chloro-2-fluorophenyl)-2,3,4,5,6,7-hexahydro-3-methylene-1H-isoindol-1-one Twenty-one parts of 2-(4-chloro-2-fluorophenyl)-2,3,4,5,6,7-hexahydro-3-hydroxy-3-methyl-1H-isoindol-1-one and one part of potassium bisulfate were heated with occasional stirring in an oil bath at 160°–170° for 15 minutes. The melt was poured into 200 parts of chloroform and washed successively with 100 parts of water, 50 parts of 10% aqueous sodium hydroxide and 100 parts of saturated aqueous sodium chloride solution. After drying the organic phase with anhydrous sodium sulfate, the solvent was evaporated at 300 mm. Hg at 50°. The residue was crystallized from 100 parts of absolute ethanol to yield 10.1 parts of 2-(4-chloro-2-fluorophenyl)-2,3,4,5,6,7-hexahydro-3-methylene-1H-isoindol-1-one melting at 84.0°–85.5°.

EXAMPLE 6

Preparation of a mixture of geometric isomers of
2-(4-chloro-2-fluorophenyl)-2,3,4,5,6,7-hexahydro-3-ethylidene-1H-isoindol -1-one One part of potassium bisulfate and 25.3 parts of 2-(4-chloro-2-fluorophenyl)-2,3,4,5,6,7-hexahydro-3-hydroxy-3-ethyl-1H-isoindol-1-one were heated with occasional stirring in an oil bath at 160°–170° for 15 minutes. The melt was poured into 200 parts of chloroform and washed successively with 100 parts of water, 50 parts of 10% aqueous sodium chloride solution and 100 parts of saturated aqueous sodium chloride solution. After drying the organic phase with anhydrous sodium sulfate, the solvent was evaporated at 300 mm. Hg at 50° to 22.3 parts of brown, glassy 2-(4-chloro-2-fluorophenyl) -2,3,4,5,6,7-hexahydro-3-ethylidene-1H-isoindol-1-one. The mixture of geometric isomers present was indicated by the absorption in the nuclear magnetic resonance spectrum of 5.1$\delta$ (1H, singlet vinyl proton) and 0.95$\delta$ (3H, singlet vinyl proton) and 1.3$\delta$ (1H, singlet vinyl proton) and 1.3$\delta$ (3H, singlet allylic methyl) for the isomer present in 40% of the total mixture.

The following compounds can be prepared by starting with the appropriately substituted 2-aryl-2,3,4,5,6,7-hexahydro-3-hydroxy-3-alkyl-1H-isoindol-1-one:

2-(4-chloro-2-fluorophenyl)-2,3,4,5,6,7-hexahydro-3-propylidene -1H-isoindol-1-one 2-(2,4,6-trifluorophenyl)-2,3,4,5,6,7-hexahydro-3-(1-methylpentylidene) -1H-isoindol-1-one 2-(4-bromophenyl)-2,3,4,5,6,7-hexahydro-3-(1-methylethylidene)-1H-isoindol-1-one 2-(4-chlorophenyl)-2,3,4,5,6,7-hexahydro-3-methylene-1H-isoindol-1-one 2-(2,4-difluorophenyl)-2,3,4,5,6,7-hexahydro-3-butylidene-1H-isoindol-1-one 2-(4-bromo-2-fluorophenyl)-2,3,4,5,6,7-hexahydro-3-methylene-1H-isoindol-1-one 2-(4-fluorophenyl)-2,3,4,5,6,7-hexahydro-3-pentylidene-1H-isoindol-1-one

EXAMPLE 7

Preparation of 2-(4-chloro-2-fluorophenyl)-3-methylene-2H-isoindol-1-one

A mixture of 8.2 parts of 2-acetylbenzoic acid, 7.27 parts of 4-chloro-2-fluoroaniline and 0.01 part of p-toluene-sulfonic acid was heated in an oil bath with occasional stirring at 150°–170° for 2 hours. The melt was poured into 100 parts of chloroform and washed successively with 50 parts of 10% aqueous hydrochloric acid solution, 50 parts of 10% aqueous sodium carbonate solution and 100 parts of a saturated aqueous sodium chloride solution. After drying the organic phase with anhydrous sodium sulfate, the solvent was evaporated at 300 mm. Hg at 50° C and the residue was crystallized from 100 parts of methanol to yield 8 parts of 2-(4-chloro-2-fluorophenyl)-3-methylene-1H-isoindol-1-one melting 86°–87°.

The following compounds can be prepared by substituting the appropriate 2-acylbenzoic acid for 2-acetylbenzoic acid and the appropriate aniline:

2-(4-bromo-2-fluorophenyl)-3-methylpentylidene-1H-isoindol-1-one 2-(2,4,6-trifluorophenyl)-3-propylidene-1H-isoindol-1-one 2-(2,4-difluorophenyl)-3-(1-methylethylidene)-1H-isoindol-1-one Useful formulations of the compounds of Formula I and IIa and IIb can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following proportions:

|  | Percent by Weight | | |
| --- | --- | --- | --- |
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredients can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corpl., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are preferred by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be used by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th Edn., McGraw-Hill, N.Y., 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.
R.W. Luckenbaugh, U.S. Pat. No. 3,309,192, March 14, 1967, Col. 5 Line 43 through Col. 7 Line 62 and Ex. 8, 12, 15, 39, 41, 52, 53, 58, 132, 138–140, 162–164, 166, 167, 169–182.
H. Gysin and E. Knusli, U.S. Pat. No. 2,891,855, June 23, 1959, Col. 3 Line 66 through Col. 5 Line 17 and Examples 1–4.
G. C. Klingman, "Weed Control as a Science", John Wiley & Sons, Inc., New York, 1961 pp. 81–96.
J. D. Fryer and S. A. Evans, "Weed Control Handbook", 5th Edn. Blackwell Scientific Publications, Oxford, 1968, pp. 101–103.

EXAMPLE 8

Granule

| 2-(4-chloro-2-fluorophenyl)-2,3,4,5,6,7-hexahydro-3-methylene-1H-isoindol-1-one attapulgite granules (low volatile matter, 0.71/0.30 mm, U.S.S. No. 25–50 sieves) | 1% |
| --- | --- |
|  | 99% |

The active ingredient was warmed to approximately 90° C and sprayed upon dedusted and pre-warmed attapulgite granules in a double cone blender. The granules were then allowed to cool and were packaged.

EXAMPLE 9

Solution

| 2-(2,4,6-trifluorophenyl)-2,3,4,5,6,7-hexahydro-3-methylene-1H-isoindol-1-one | 5% |
| --- | --- |

-continued

| | |
|---|---|
| dimethylformamide | 95% |

Mixing of the ingredients was by conventional means.

EXAMPLE 10

Emulsifiable Concentrates

| | |
|---|---|
| 2-(4-chloro-2-fluorophenyl)-2,3,4,5,6,7-hexahydro-3-methylene-1H-isoindol-1-one | 25% |
| blend of oil soluble sulfonates and polyoxyethylene ethers | 8% |
| xylene | 67% |

The ingredients were combined and stirred with gentle warming to speed solution. A fine screen filter was included in the packaging operation to insure the absence of any extraneous undissolved material in the product.

EXAMPLE 11

Wettable Powder

| | |
|---|---|
| 2-(4-chloro-2-fluorophenyl)-2,3,4,5,6,7-hexahydro-3-hydroxy-3-methyl-1H-isoindol-1-one | 40% |
| dioctyl sodium sulfosuccinate | 1.5% |
| sodium ligninsulfonate | 3% |
| low viscosity methyl cellulose | 1.5% |
| attapulgite | 54% |

The ingredients were thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 12

High Strength Concentrate

| | |
|---|---|
| 2-(2,4,6-trifluorophenyl)-2,3,4,5,6,7-hexahydro-3-methylene-1H-isoindol-1-one | 98.5% |
| silica aerogel | 0.5% |
| synthetic amorphous fine silica | 1.0% |

The ingredients were blended and ground in a hammermill to produce a high strength concentrate essentially all passing a U.S.S. No. 50 sieve (0.3 mm openings). This material may then be formulated in a variety of ways.

Utility

The compounds of formula I, IIa and IIb are useful for the selective preemergence weed control of undesired vegetation in crops such as rice, soybeans, peanuts, lima beans, sugarbeets, corn, green beans and squash. The compounds of this invention also can be used as directed treatments for the pre/post-emergence control of weeds in various crops including soybeans, peanuts, garden beans and row-planted rice. In addition, these compounds are useful wherever general weed control is required, such as industrial sites, railroad and utility rights-of-way, along fences, builing foundations, parking and storage lots, etc.

The precise amount of the compounds of Formula I and IIa and IIb to be used in any given situation will vary according to the particular end result desired, the plant species and soil involved, the formulation used, the mode of application, prevailing weather conditions, foliage density and like factors. Since so many variables play a role, it is not possible to state a rate of application suitable for all situations. Broadly speaking, the compounds of the invention are used at levels of about 0.125 to about 20 kilograms, preferably about 0.25 to about 10, per hectare. The lower rates in this range will generally be selected on lighter soils, soils low in organic matter content, for selective weed control in crops, or in situations where maximum persistance is not necessary.

Herbicidal activity of compounds of this invention was discovered in a greenhouse test.

Combinations with other herbicides may be useful in many situations.

TEST DESCRIPTION

Seeds of soybean, corn, cotton, rice, wheat, sorghum, alfalfa, barnyardgrass (*Echinochloa crusgalli*), giant foxtail (*Setaria faberii*), morningglory (*Ipomoea hederacea*), velvetleaf (*Abutilon theophrasti*), sesbania (*Sesbania* sp.), cassia (*Cassia tora*), cocklebur (*Xanthium pennsylvanicum*), nutsedge (*Cyperus rotundus*), crabgrass (*Digitaria sanguinalis*), jimsonweed (*Datura stramonium*), and wild oats (*Avena fatua*) were planted in greenhouse soil and allowed to grow for 14 days. At this time, the treatments were applied over the top of the crops and weeds in a nonphytotoxic solvent containing a wetting plant. Fourteen days after treatment, the plants were evaluated and the data below recorded in Table 1.

| |
|---|
| Zero = no response |
| 10 = maximum response |
| C = chlorosis necrosis |
| B = burn |

TABLE 1

| | Fallsington Sandy Loam Compound | | | | | | | |
|---|---|---|---|---|---|---|---|---|
| | 2-(4-chloro-2-fluorophenyl)-2,3,4,5,6,7-hexahydro-3-methylene-1H-isoindol-1-one | | 2-(4-chloro-2-fluorophenyl)-2,3,4,5,6,7-hexahydro-3-hydroxy-3-methyl-1H-isoindol-1-one | | 2-(4-chloro-2-fluorophenyl)-2,3,4,5,6,7-hexahydro-3-ethylidene-1H-isoindol-1-one —60:40 mixture of geometric isomers | | 2-(4-chloro-2-fluorophenyl) 2,3,4,5,6,7-hexahydro-3-propylidene-1H-isoindol-1-one — 60:40 mixture of geometric isomers | |
| Rate, kg/ha | 1/8 | 1/2 | 1/8 | 1/2 | 1/8 | 1/2 | 1/8 | 1/2 |
| Soybeans | 5B | 6B | 4B | 5B | 3B | 6B | 3B | 4B |
| Velvetleaf | 10B | 10B | 9B | 10B | 7B | 10B | 9B | 10B |
| Sesbania | 7B | 10B | 6B | 8B | 5B | 7B | 6B | 7B |
| Cassia | 6B | 6B | 4B | 5B | 4B | 4B | 5B | 6B |

TABLE 1-continued

| | Fallsington Sandy Loam Compound | | | | | | | |
|---|---|---|---|---|---|---|---|---|
| | 2-(4-chloro-2-fluoro-phenyl)-2,3,4,5,6,7-hexahydro-3-methylene-1H-isoindol-1-one | | 2-(4-chloro-2-fluoro-phenyl)-2,3,4,5,6,7-hexahydro-3-hydroxy-3-methyl-1H-isoindol-1-one | | 2-(4-chloro-2-fluorophenyl)-2,3,4,5,6,7-hexahydro-3-ethylidene-1H-isoindol-1-one —60:40 mixture of geometric isomers | | 2-(4-chloro-2-fluorophenyl)2,3,4,5,6,7-hexahydro-3-propylidene-1H-isoindol-1-one — 60:40 mixture of geometric isomers | |
| Cotton | 9B | 10B | 9B | 6B | 7B | 9B | 9B | 9B |
| Morningglory | 6B | 8B | 4B | 6B | 6B | 6B | 4B | 6B |
| Alfalfa | 6B | 7B | 4B | 5B | 3B | 6B | 4B | 4B |
| Jimsonweed | 9B | 10B | 9B | 10B | 7B | 10B | 10B | 10B |
| Cocklebur | 4B | 7B | 3B | 4B | 3B | 6B | 6B | 4B |
| Corn | 3B | 5B | 3B | 4B | 3B | 3B | 4B | 4B |
| Crabgrass | 5B | 3B | 2C | 5B | 2B | 5B | 3B | 6B |
| Rice | 4B | 6B | 3B | 5B | 2B | 6B | 3B | 4B |
| Nutsedge | 3B | 4B | 0 | 2B | 0 | 2B | 2B | 3B |
| Barnyardgrass | 3B | 4B | 3B | 4B | 3B | 3B | 3B | 4B |
| Wheat | 3B | 4B | 2C | 4B | 2C | 3B | 3C | 4C |
| Giant Foxtail | 5B | 5B | 5B | 6B | 4B | 6B | 4B | 5B |
| Wild Oats | 4C | 5B | 2C | 3B | 3B | 2C | 4C | 5B |
| Sorghum | 4B | 4B | 4B | 4B | 3B | 3C | 3B | 5B |

The above table illustrates the effectiveness of compounds of the instant invention against undesired vegetation such as velvetleaf when applied postemergence. At the same time, relatively minor damage is done to crops such as wheat.

DESCRIPTION

Two plastic bulb pans were filled with fertilized and limed Fallsington sandy loam. One pan was planted with corn, sorghum and several grassy weeds. The other pan was planted with soybeans, purple nutsedge (*Cyperus rotundus*), and several broadleaf weeds. The following grassy and broadleaf weeds were planted: carbgrass (*Digitaria crusgalli*), wild oats (*Avena fatua*), johnsongrass (*Sorghum halepense*), giant foxtail (*Setaria faberii*), Kentucky bluegrass (*Poa pratensis*), cheatgrass (*Bromus secalinus*), mustard (*Brassica arvensis*), cocklebur (*Xanthium pennsylvanicum*), pigweed (*Amaranthus retroflexus*), curly indigo (*Aeschynomene virginica*), morningglory (*Ipomoea hederacea*), cassia (*Cassia tora*), teaweed (*Sida spinosa*), velvetleaf (*Abutilon theophrasti*), and jimsonweed (*Datura stramonium*). A 5-inch diameter plastic pot was also filled with prepared soil and planted with rice and wheat. A 4-inch pot was planted with sugarbeets. The above four containers were treated preemergence (compound sprayed on soil surface before seed germination).

Twenty-eight days after treatment, the plants were evaluated and the data below recorded in Table 2.

```
Zero = no response
  10 = maximum response
   C = chlorosis necrosis
   G = growth retardation
   H = formative effect
   E = emergence inhibition
```

TABLE 2

| | Fallsington Sandy Loam Compound | | | | | | |
|---|---|---|---|---|---|---|---|
| | 2-4-chloro-2-fluoro phenyl)-2,3,4,5,6,7-hexahydro-3-methylene-1H-isoindol-1-one | | 2-(4-chloro-2-fluoro-phenyl)-2,3,4,5,6,7-hexahydro-3-hydroxy-3-methyl-1H-isoindol-1-one | | 2-(4-chloro-2-fluoro-phenyl)-2,3,4,5,6,7-hexahydro-3-ethylidene-1H-isoindol-1-one —60:40 mixture of geometric isomers | | |
| Rate, kg/ha | 1/8 | 1/2 | 1/8 | 1/8 | 1/2 | 1/8 | 1/2 |
| Crabgrass | 10C | 10C | 10H | 0 | 10C | 0 | 10E |
| Barnyardgrass | 2G | 9H | 3C | 0 | 3C | 0 | 7H |
| Sorghum | 5H | 10H | 4H | 0 | 5H | 0 | 6H |
| Wild Oats | 0 | 4H | 2H | 0 | 3H | 0 | 3H |
| Johnsongrass | 2H | 10E | 5H | 0 | 7H | 0 | 8H |
| Giant Foxtail | 2H | 10E | 8H | 0 | 7H | 0 | 4H |
| Ky. bluegrass | 3H | 10E | 8H | 0 | 9H | 0 | 5H |
| Cheatgrass | 0 | 7H | 2H | 0 | 3H | 0 | 2H |
| Corn | 0 | 4C | 0 | 0 | 0 | 0 | 0 |
| Mustard | 0 | 3G | 3C | 0 | 7G | 0 | 6G |
| Cocklebur | 0 | 3G | 0 | 0 | 5G | 0 | 0 |
| Pigweed | 4C | 9C | 4H | 0 | 10C | 0 | 10C |
| Nutsedge | 0 | 0 | 0 | 0 | 0 | 0 | 2C |
| C. indigo | 10C | 10C | 10E | 0 | 10C | 0 | 10C |
| Morningglory | 0 | 0 | 0 | 0 | 3H | 0 | 0 |
| Cassia | 0 | 0 | 0 | 0 | 0 | 0 | 0 |
| Teaweed | 0 | 8C | 10E | 0 | 0 | 0 | 8C |
| Velvetleaf | 0 | 4C | 10C | 0 | 0 | 0 | 5C |
| Jimsonweed | 0 | 8C | 5C | 0 | 5H | 0 | 5H |
| Soybean | 0 | 0 | 0 | 0 | 2C | 0 | 0 |
| Rice | 0 | 4H | 0 | 0 | 0 | 0 | 2H |
| Wheat | 0 | 3H | 0 | 0 | 0 | 0 | 0 |
| Sugarbeets | 0 | 9C | 0 | 0 | 0 | 0 | 0 |

The corn, table illustrates the effectiveness of compounds of the instant invention against numerous weeds when applied preemergence. At the same time, relatively little or no damage is done to desirable crops such as wheat, corn, soybeans, sugarbeets, and rice.

What is claimed is:

1. A compound of the formulae

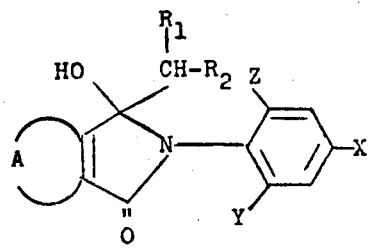

Formula I

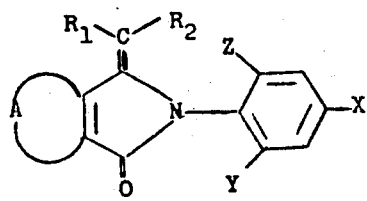

Formula IIa or

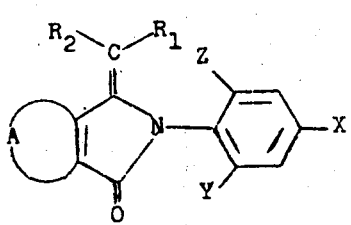

Formula IIb

Wherein $R_1$ is hydrogen or methyl;
$R_2$ is hydrogen or alkyl of 1 to 4 carbons;
X is fluorine, chlorine or bromine;
Y is hydrogen or fluorine;
Z is hydrogen or fluorine, provided that when Y and Z are both fluorine, X must also be fluorine; and
A is $-(CH_2)_4-$ or $-CH=CH-CH=CH-$, provided that when A is $-CH=CH-CH=CH-$ and Y is hydrogen, Z must be fluorine.

2. A compound of claim 1 wherein either Formula IIa or Formula IIb is utilized.

3. A compound of claim 2 wherein z is fluorine and A is $-(CH_2)_4-$.

4. A compound of claim 3 wherein $R_1$ is hydrogen.

5. A compound of claim 4 wherein $R_2$ is hydrogen.

6. The compound 2-(4-chloro-2-fluorophenyl)-2,3,4,5,6,7-hexahydro-3-methylene-1H-isoindol-1-one.

7. A composition for the control of undesirable vegetation consisting essentially of a compound of claim 1 and at least one of (a) surface-active agent and (b) a solid or liquid diluent.

8. A composition for the control of undesirable vegetation consisting essentially of a compound of claim 2, and at least one of (a) a surface-active agent and (b) a solid or liquid diluent.

9. A composition for the control of undesirable vegetation consisting essentially of a compound of claim 3, and at least one of (a) a surface-active agent and (b) a solid or liquid diluent.

10. A composition for the control of undesirable vegetation consisting essentially of a compound of claim 4, and at least one of (a) a surface-active agent and (b) a solid or liquid diluent.

11. A composition for the control of undesirable vegetation consisting essentially of a compound of claim 5 and at least one of (a) a surface-active agent and (b) a solid or liquid diluent.

12. A composition for the control of undesirable vegetation consisting essentially of the compound of claim 6, and at least one of (a) a surface-active agent and (b) a solid or liquid diluent.

13. A method for the control of undesirable vegetation comprising applying to the locus of such undesired vegetation a herbicidally effective amount of a compound of claim 1.

14. A method for the control of undesirable vegetation comprising applying to the locus of such undesired vegetation a herbicidally effective amount of a compound of claim 2.

15. A method for the control of undesirable vegetation comprising applying to the locus of such undesired vegetation a herbicidally effective amount of a compound of claim 3.

16. A method for the control of undesirable vegetation comprising applying to the locus of such undesired vegetation a herbicidally effective amount of a compound of claim 4.

17. A method for the control of undesirable vegetation comprising applying to the locus of such undesired vegetation a herbicidally effective amount of a compound of claim 5.

18. A method for the control of undesirable vegetation comprising applying to the locus of such undesired vegetation a herbicidally effective amount of the compound of claim 6.

* * * * *